United States Patent [19]
Leise, Jr. et al.

[11] Patent Number: 5,947,941
[45] Date of Patent: Sep. 7, 1999

[54] TWO-PIECE OSTOMY APPLIANCE

[75] Inventors: Walter F. Leise, Jr., Lindenhurst; Michael A. Metz, Chicago; James J. Peterson, Island Lake, all of Ill.

[73] Assignee: Hollister Incorporated, Libertyville, Ill.

[21] Appl. No.: 09/035,584

[22] Filed: Mar. 5, 1998

[51] Int. Cl.$^6$ .................................................. A61F 5/445
[52] U.S. Cl. ........................ 604/338; 604/339; 604/332
[58] Field of Search ................................ 604/338, 339, 604/342, 332

[56] References Cited

U.S. PATENT DOCUMENTS

| | | | |
|---|---|---|---|
| 4,872,869 | 10/1989 | Johns | 604/342 |
| 5,185,008 | 2/1993 | Lavender | 604/338 |
| 5,195,996 | 3/1993 | Edwards et al. | 604/338 |
| 5,520,670 | 5/1996 | Blum | 604/338 |
| 5,693,036 | 12/1997 | Kilgour | 604/338 |

FOREIGN PATENT DOCUMENTS 0 163 979  11/1985  European Pat. Off. .
0 463 359  1/1992  European Pat. Off. .

*Primary Examiner*—Robert A. Clarke
*Assistant Examiner*—Catherine Cogut
*Attorney, Agent, or Firm*—Tilton Fallon Lungmus

[57] ABSTRACT

A two-piece ostomy appliance is disclosed, one component being a collection pouch and the other an adhesive faceplate for peristomal attachment to a patient. The two components are provided with coupling rings for mechanically and detachably joining them together. One of the rings has a bead-providing collar and a rocking wedge body as disclosed in U.S. Pat. No. 5,185,008. The other ring is of channel-shaped cross section having spaced concentric inner and outer side walls each provided with ribs positioned in direct opposition and extending into the channel along a single plane normal to the axis of that ring. In a preferred embodiment, the rib of the outer wall is interrupted to provide at least one wide notch or recess and an integral pull tab projects radially outwardly from the outer wall at the location of the notch for initiating either partial or complete separation of the rings during use of the appliance.

23 Claims, 3 Drawing Sheets

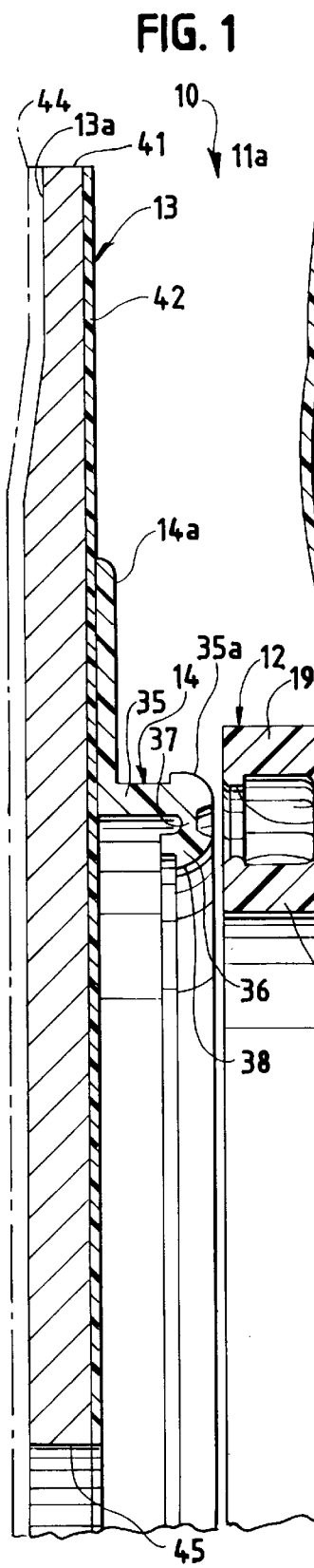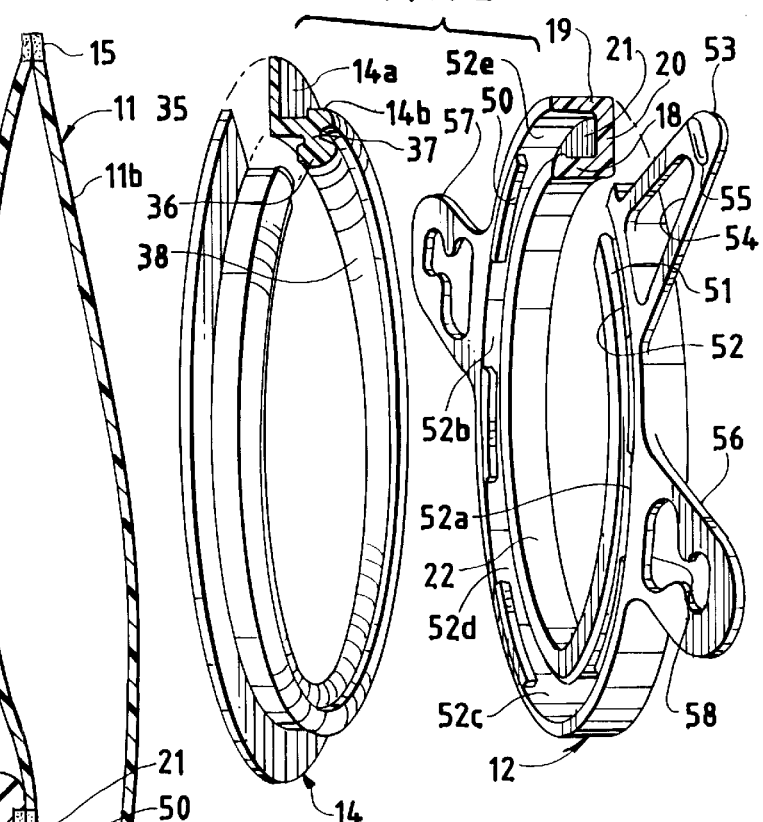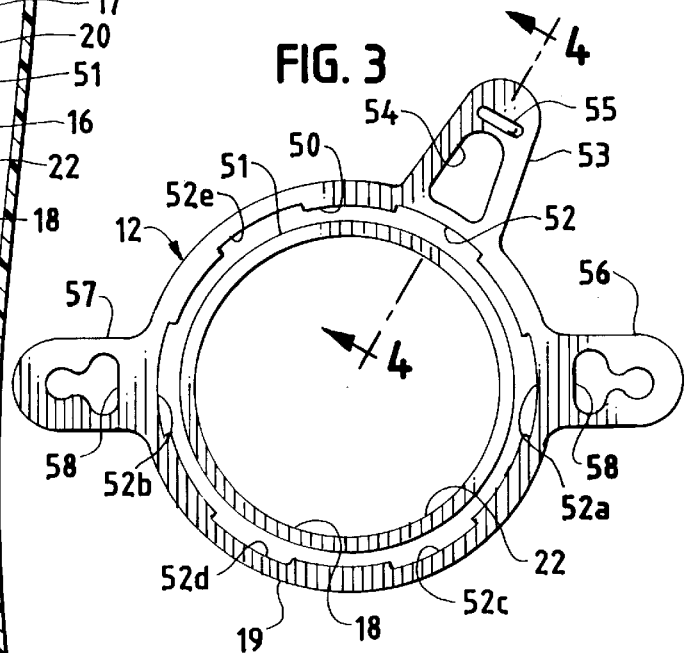

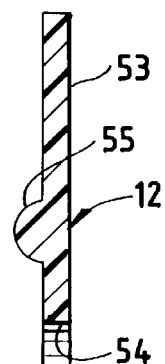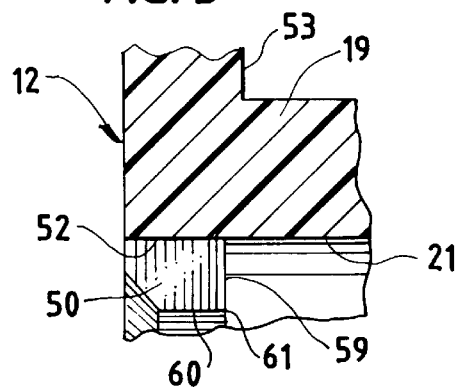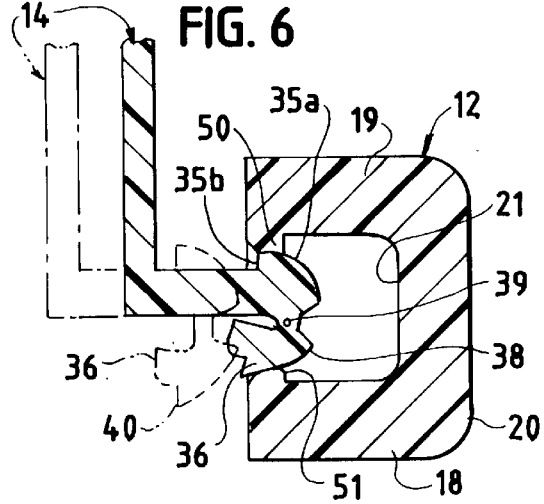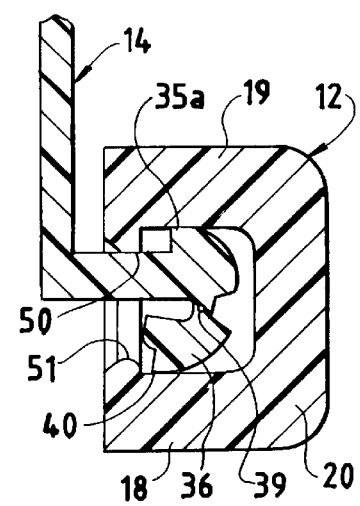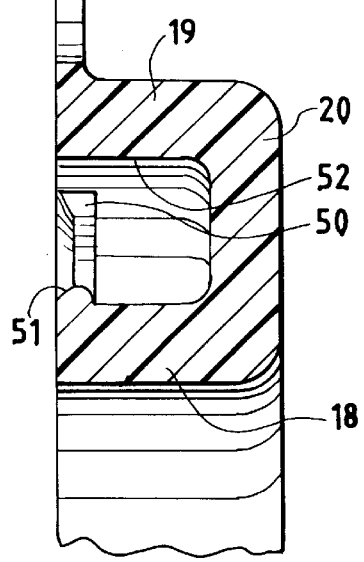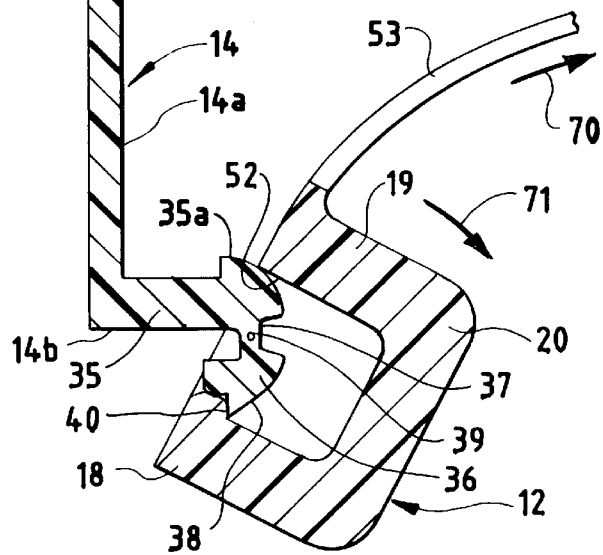

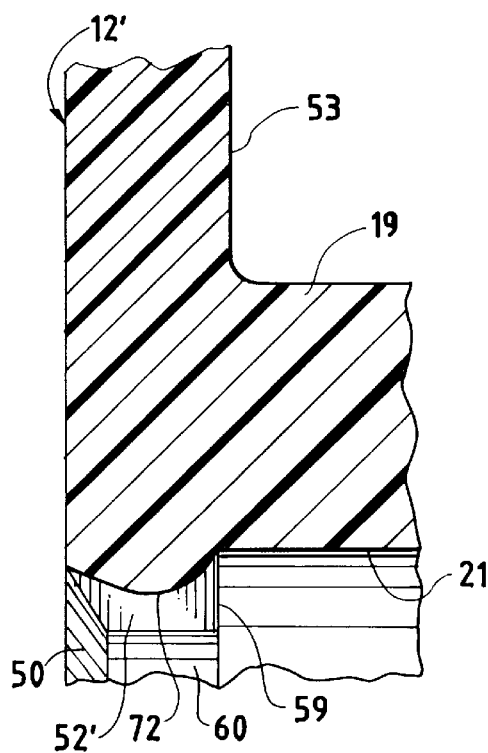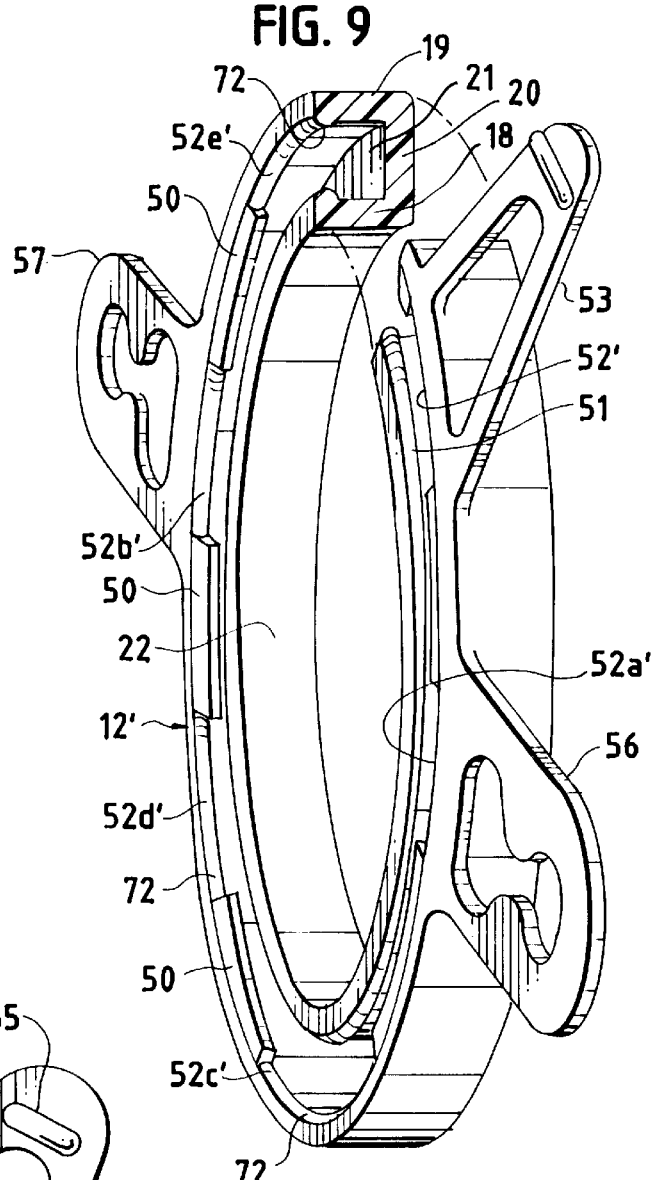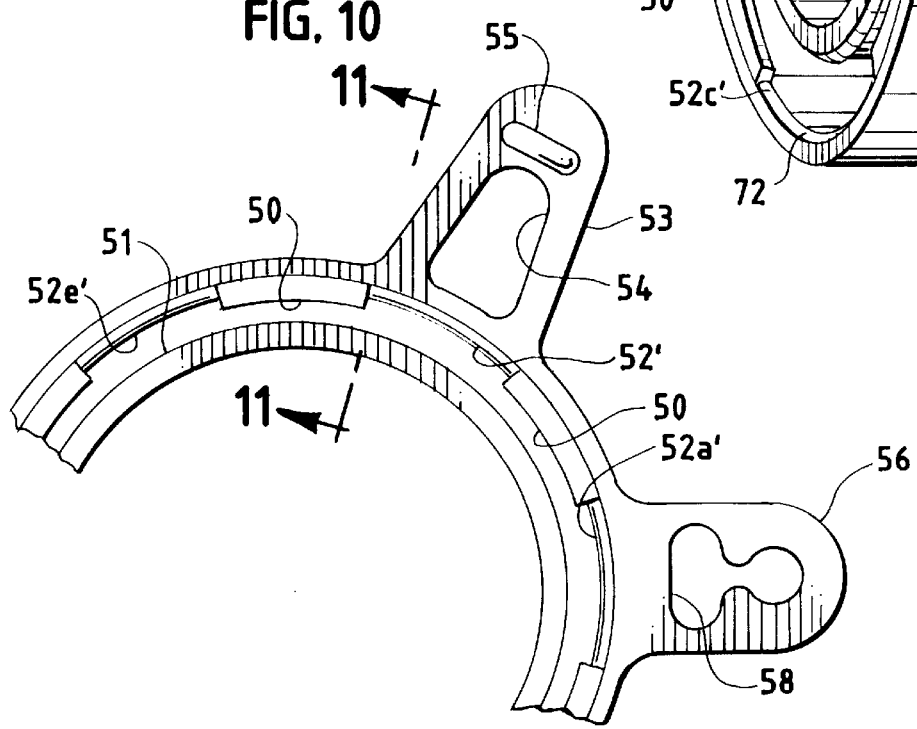

TWO-PIECE OSTOMY APPLIANCE

BACKGROUND AND SUMMARY

U.S. Pat. No. 5,185,008 discloses a two-piece ostomy appliance in which one of the coupling rings is channel shaped and the other is provided with a substantially non-compressible insert that includes an axially-extending collar, a non-deformable wedge body, and a radially-extending pivot stem that centrally connects the collar and wedge body. The pivot stem allows limited forward and rearward rocking movement of the wedge body about a pivot axis extending through the stem. A massive front portion of the wedge body has an inwardly and rearwardly curved bearing surface of progressively increasing distance from the pivot axis so that the radial width of the insert decreases as the wedge body rocks rearwardly and increases as it rocks forwardly about the pivot axis. Ease of coupling is enhanced because rearward rocking of the wedge body decreases the width of the insert as it is being advanced into the channel of the other ring, and greater security is insured because forward rocking of the wedge body during the initial stages of ring separation effectively increases the radial width of the insert and thereby increases the resistance to ring separation.

Other references disclosing the state of the art are U.S. Pat. Nos. 4,872,869, 5,185,008, and 5,195,996, and European patent 0 463 359.

One aspect of this invention lies in providing a modified rocking wedge lock for the coupling rings of a two-piece ostomy appliance in which the rings, when coupled, are of relatively low profile and yet provide a highly secure locking and sealing action. In contrast to the construction disclosed in U.S. Pat. No. 5,185,008, the rings embodying this invention emit a clearly audible snapping or clicking sound as they are joined together, thereby signaling to the user that a secure and complete interconnection has been achieved.

The security of the interlock results partly from the fact that the walls of the channel-shaped coupling ring are relatively thick and resist outward flexure when the insert portion of the other locking ring, with its rocking wedge body, is inserted into the channel. In addition, the thick inner and outer side walls are of substantially the same length and have directly opposing rib means projecting into the channel at its entrance. The rib means of the outer wall is engagable with a bead along the collar portion of the insert element of the other ring and the rib means of the inner wall is engagable with a shoulder of the rocking wedge body, causing a forward rocking and wedging action of that body when axial forces of separation are applied to the rings. However, when a twisting force is selectively applied to the channel-shaped ring, with such force being exerted by pulling a tab extending radially outwardly from the channel ring's outer wall, such twisting may selectively initiate partial or complete uncoupling of the rings. Partial uncoupling may be used to vent and deflate a pouch of flatus gases, whereas complete uncoupling is undertaken when a pouch is to be removed and replaced, usually by a fresh pouch.

The rib means projecting into the channel from the inner wall is continuous and uninterrupted but, in preferred embodiments of the invention, the rib means of the outer wall is interrupted to define a notch or recess along an arcuate stretch in direct alignment with the pull tab. The channel ring may be provided with a plurality of such pull tabs, arranged in a circumferentially-spaced relation, in which case the rib means of the outer wall should have a plurality of notches, each pull tab being directly aligned with one of the notches. If desired, the rib means of the outer wall may have a multiplicity of uniformly-spaced notches about the full circumference of the wall with certain of such notches occurring even where no pull tabs are located.

The rib means of the outer wall adjacent each notch are preferably sharply undercut rather than rounded when viewed in radial section. More specifically, the rib of the outer wall has a rear surface that faces the channel and lies along a generally radial plane, an inner surface that faces inwardly towards the axis of the coupling ring, and an edge, preferably sharply defined, at the junction of the two surfaces. The sharply undercut surface of the rib latches against the bead of the other coupling ring (which is also sharply undercut) to enhance latching security as well as contribute in producing an audible clicking or snapping sound as the rings are coupled together.

In one preferred embodiment, each notch in the rib means of the outer wall has an inwardly facing surface that is flush with the remainder of the surface of the outer wall within the channel, thus resulting in a construction in which the wall is smooth and ribless for the full width of the notch. Since the notch is in direct alignment with a pull tab and preferably has a width or angular dimension approximating that of the tab, the notch facilitates intentional uncoupling of the rings when the channel-shaped ring is twisted in response to a pulling force applied to the tab. Full or partial disconnection of the rings commences when the bead of the faceplate ring slides out of the channel through the opening defined by the notch. The same result may be achieved by a second preferred embodiment in which the surface of each notch is not flush with that of the outer surface of the channel but instead is provided with a rounded shoulder of lesser height (measured radially) than the sharply undercut rib portions adjacent the notch.

Other features, advantages, and objects of the invention will become apparent from the specification and drawings.

DRAWINGS

FIG. 1 is a vertical sectional view illustrating an ostomy appliance embodying this invention and illustrating the parts in uncoupled condition.

FIG. 2 is an exploded perspective view of the coupling rings with the pouch and faceplate omitted and with sections of the rings removed to illustrate the cross sectional configuration of the parts.

FIG. 3 is a plan view of the channel-shaped coupling ring embodying this invention.

FIG. 4 is an enlarged sectional view taken along line 4—4 of FIG. 3.

FIG. 5 is a greatly enlarged fragmentary sectional view taken along line 5—5 of FIG. 3.

FIG. 6 is a somewhat schematic fragmentary sectional view illustrating the action of the rocking wedge lock as the two rings are urged together.

FIG. 7 is a fragmentary sectional view similar to FIG. 5 but showing the rings in fully coupled condition.

FIG. 8 is a somewhat schematic sectional view showing the channel-shaped coupling ring sectioned through a pull tab and depicting the twisting action of that ring during the initiation of a venting or uncoupling operation.

FIG. 9 is a perspective view of a coupling ring constituting a second embodiment of the invention, a section of the ring being removed to illustrate the cross section of the ring.

FIG. 10 is a fragmentary plan view of the coupling ring of FIG. 9.

FIG. 11 is a greatly enlarged fragmentary sectional view taken along line 11—11 of FIG. 10.

DETAILED DESCRIPTION OF PREFERRED EMBODIMENTS

Referring to FIG. 1 of the drawings, the numeral 10 generally designates a two-piece ostomy appliance, one component constituting a collection pouch 11 with a first coupling ring 12 and the other comprising a faceplate 13 equipped with a second coupling ring 14. As shown, pouch 11 is formed of two sheets 11a and 11b of thermoplastic material heat sealed together along their edges 15. The pouch may be provided with a drain outlet at its lower end which may be closable by a suitable clamping device (not shown), such as the one disclosed in U.S. Pat. No. 3,523,534, or it may be sealed at its lower end, effectively rendering the pouch non-drainable. One wall 11a of the pouch has a side opening 16 with the first coupling ring 12 concentrically heat sealed at 17 to the outer surface of the pouch wall about that opening.

Pouch coupling ring 12 is channel-shaped in cross section, having a pair of concentric inner and outer side walls 18 and 19 joined by a connecting wall 20. The annular channel 21 defined by the ring 12 faces in an axial direction away from pouch 11. Opening 22 of the ring aligns with the stoma opening 16 of the pouch. In the respects so far described, pouch coupling ring 12 is similar to the pouch ring disclosed in U.S. Pat. No. 5,185,008 except that it is lower in profile and its side walls 18, 19 and connecting wall 20 are relatively thick and unyielding.

The second coupling ring 14 of faceplate 13 is similar to the faceplate ring of the aforementioned patent. Like pouch ring 12, the faceplate ring 14 is formed of a semi-rigid thermoplastic material such as low-density polyethylene. Ring 14 includes a planar, radially and outwardly extending flange portion 14a and an integral axially-extending insert portion 14b. The insert portion comprises an axially-extending cylindrical collar 35 having an outwardly extending bead 35a, a bulbous non-deformable wedge body 36 of toroidal shape, and an annular, radially-extending pivot stem 37. The stem is integrally formed with the collar and wedge body and connects the two in concentric relation, with the stem being generally centrally disposed in relation to the wedge body.

As described in U.S. Pat. No. 5,185,008, the disclosure of which is incorporated by reference herein, the wedge body 36 has an inwardly and rearwardly curved bearing surface 38 of progressively increasing distance from a pivot axis 39 located in or at stem 37 and diagramatically represented in FIGS. 5–7. The radius of curvature of surface 38 measured from pivot axis 39 increases gradually and progressively as the surface curves rearwardly and inwardly from the forward limits of the wedge body. The curved bearing surface continues rearwardly and radially inwardly to an annular shoulder or edge 40 along the rear limits of bearing surface 38. Shoulder 40 therefore defines the innermost limits of the annular insert means 14b.

The flange portion 14a of the second coupling ring 14 may be secured to the adhesive wafer 13a of the faceplate by any suitable means. In the embodiment illustrated, wafer 13a may be formed of a hydrocolloid-containing adhesive layer 41 covered on its pouchside surface by a flexible thermoplastic film 42. Flange portion 14a may be heat sealed or adhesively joined to film 42. A release sheet 44, formed of siliconized paper or a polymeric film such as polyethylene terephthalate, is shown in phantom in FIG. 1 and is intended to be peeled away from the surface of adhesive layer 41 when the faceplate is to be applied to the peristomal skin surfaces of a wearer. A starter opening 45 is provided in the central portion of the adhesive wafer 13a and may be enlarged (by cutting with scissors) at the time of application to match the shape and size of a patient's stoma.

As noted, adhesive layer 41 is preferably composed of a hydrocolloid-containing adhesive material, although other pressure-sensitive adhesives, such as a conventional medical-grade acrylic adhesive, may be used. Where a hydrocolloid-containing adhesive is selected, its composition may be any of a variety of known "skin barrier" adhesives available for use with ostomy products. Such skin barrier compositions typically contain hydrocolloid particles dispersed throughout a continuous elastomeric adhesive phase. Compositions suitable for this purpose are described in U.S. Pat. No. 5,492,943, the disclosure of which is incorporated by reference herein, and in the earlier patents discussed in the specification thereof.

The pouch coupling ring 12 has directly-opposing first and second rib means 50 and 51 located at the entrance to channel 21. The opposing ribs lie along a single plane normal to the axis of the ring, and the spacing between the opposing ribs is substantially less than the radial width of the insert portion 14b of the second ring 14 when the wedge body is not pivoted rearwardly, that is, when the wedge body is in the unpivoted position depicted in FIGS. 1 and 2 and in broken lines in FIG. 6.

Rib 51 of inner wall 18 is continuous and uninterrupted, as shown most clearly in FIGS. 2 and 3, but the rib 50 of the outer wall 19 is interrupted to define at least one notch or recess 52. The angular length of the notch may fall generally within the range of about 20 to 60 degrees and preferably about 30 to 45 degrees. In the particular embodiment shown in FIGS. 1–8, the angular length is about 30 degrees.

A pull tab 53 is formed integrally with channel-shaped ring 12 and projects radially outwardly from outer wall 19 at the location of notch 52. The width of the tab where it merges with the outer wall approximates the width of the notch and, if desired, the tab portion may be tapered outwardly as depicted in FIGS. 2 and 3. An opening 54 and one or more projections 55 may be formed in the tab to reduce slippage between the fingers when the tab is pulled, with the opening also performing the function of increasing the flexibility of the tab.

While the operational benefits hereinafter described may be achieved with a channel-shaped coupling ring 12 having only a single notch or recess 52 and a single pull tab 53, it is believed advantageous to provide a plurality of such notches and tabs. In the embodiment illustrated, there are two additional pull tabs 56 and 57 that are diametrically disposed and, if desired, may also be used as attachment means for a support belt (not shown). While the use of such tabs for belt attachment is conventional, their location in direct alignment with notches 52a and 52b, in the same physical relationship that exists between tab 53 and notch 52, is believed distinctive both structurally and functionally.

The notches 52a and 52b are shown in FIG. 3 to be of the same angular length as notch 52 although, if desired, such notches may be of different lengths. Also, the provision of additional notches 52c, 52d and 52e, resulting in a series of uniformly-spaced notches and a plurality of rib segments of uniform length therebetween, has manufacturing and aesthetic advantages but is not critical to enhancing the functional benefits of the invention.

Tabs 56 and 57 have conventional openings for receiving the buttons or hooks of a support belt (not shown). For purposes of this invention, such openings also provide advantages similar to those described with regard to opening 54 of pull tab 53. Specifically, openings 58 increase the flexibility of tabs 56 and 57 and reduce the possibilities of slippage when the tabs are gripped between the fingers and pulled forwardly when separation of the rings 12 and 14 is desired.

Referring to FIG. 5, rib 50 is shown to be sharply undercut, having a rear surface 59 facing into the channel of ring 12 and lying along a generally radial plane and an inner surface 60 facing inwardly towards the axis of the ring, the two surfaces meeting along an edge 61. Notch 52 (as well as all other notches formed in the outer rib of ring 12) has its surface flush with the inner surface of wall 19 within channel 21 (FIG. 5).

During a coupling operation, wedge body 36 rocks rearwardly as its curved surface rides over annular rib 51 (FIG. 6). Once clear of that rib, the wedge body rocks forwardly, expanding the insert means within the channel 21 of ring 12 (FIG. 7). As that occurs, bead 35a passes through the entrance to the channel and its sharply undercut back surface 35b clears rear surface 59 of rib 50. As the wedge body clears rib 51 and rocks forwardly, and the bead 35a clears the sharply undercut rib 50, an audible snapping or clicking sound is produced, signalling to the user that full insertion and latching has occurred. It is to be noted that because the walls 18–20 of the channel-shaped ring 12 are relatively heavy, no appreciable outward flexure of the side walls occurs during a coupling operation.

The provision of opposing rib means lying along a single plane at the mouth of the channel, in combination with a mating coupling ring of rocking wedge design, results in an assembly that yields high security of attachment in response to axially-directed forces of separation even where the axial dimensions of the parts are minimized to provide a low-profile coupling as shown. Referring to FIG. 7, if axial forces of separation should be applied to rings 12 and 14, wedge body rocks in a counterclockwise direction causing the shoulder 40 to engage the surface of side wall 18 even more tightly in what might be regarded as a biting action. The holding power significantly increases when shoulder 40 engages rib 51, especially because the relatively heavy walls 18–20 of the channel resist expansive deformation. Unintentional uncoupling of the rings is therefore effectively resisted despite the low-profile configuration of the parts.

Intentional uncoupling is initiated by pulling one of the pull tabs 53, 56, or 57 to cause a twisting of ring 12 as illustrated in FIG. 8. Because the force is localized, being applied to only a small arcuate portion of outer wall 19, it is believed that manual uncoupling with reasonable force might be possible even if the rib means 50 of outer wall 19 were not interrupted at the location of the pull tab. Intentional uncoupling is, however, greatly facilitated by the existence of the ribless notch 52 (or 52a or 52b) at the location of pull tab 53 (or 56 or 57). When a forward pulling force is exerted on the tab in the direction of arrow 70, channel-shaped ring is forced to twist in the direction of arrow 71 and, since the inner surface of side wall 19 is ribless in the area of the pull tab, the smooth ribless portion of that wall readily slides over bead 35a.

Once the parts have assumed the relationship depicted in FIG. 8, only slight additional twisting action is required to produce partial uncoupling of the rings for venting purposes. If additional pulling force is applied to the tab, the separation of the ring propagates circumferentially in opposite directions and results in complete uncoupling of the parts.

The preferred embodiment of FIGS. 9–11 is the same in structure and operation as the embodiment already described except that each notch 52' and 52a' through 52e' does not have its surface flush with the cylindrical inner surface of outer wall 19. Instead, a shoulder 72, having a rounded surface (when viewed in section as in FIG. 11) extends the length of each notch. It will be noted that the radial dimension or height of each shoulder is substantially less than the radial dimension or height of the rear surface 59 of rib 50.

Shoulder 72 functions as a mini-rib to increase the security of the locking action between the coupling rings where further security (over that provided by the embodiment of FIGS. 1–8) is believed desirable. Because the shoulder 72 is not sharply undercut and offers only a smoothly rounded surface for contact with the bead 35a of the bodyside coupling ring 14, the shoulder does not appreciably increase the forces to be applied to pull tab 53 (or 56 or 57) when intentional uncoupling of the parts is to be initiated in the manner described in reference to FIG. 8.

While in the foregoing we have disclosed embodiments of the invention in considerable detail for purposes of illustration, it will be understood by those skilled in the art that many of these details may be varied without departing from the spirit and scope of the invention.

We claim:

1. A coupling ring of semi-rigid thermoplastic material for attachment to the pouch of a two-piece ostomy appliance; said coupling ring being of channel-shaped cross section and having spaced concentric inner and outer side walls and a connecting wall joining said side walls;

wherein the improvement comprises said coupling ring having first rib means projecting into said channel from said outer side wall and having second rib means projecting into said channel from said inner side wall;

said first and second rib means being in direct opposition to each other and extending along a single plane normal to the axis of said coupling ring; said second rib means being annular and continuous and said first rib means being interrupted along at least one portion of said outer wall to provide a notch having an angular dimension of about 20 to 50 degrees; and an integral tab portion projecting radially outwardly from said outer wall; said notch and said tab portion being in direct alignment with each other.

2. The coupling ring of claim 1 in which said notch has an angular dimension within the range of about 30 to 45 degrees.

3. The coupling ring of claim 1 in which said side walls are of substantially equal length and define an entrance opening for the channel of said ring; said first and second rib means being located at said entrance opening.

4. The coupling ring of claim 1 in which said first rib means has a plurality of circumferentially-spaced interruptions defining a plurality of said notches; said outer wall being provided with a plurality of said radially outwardly extending tab portions; each of said tab portions being located in direct alignment with one of said notches.

5. The coupling ring of claim 4 in which two of said radially outwardly extending tab portions are diametrically disposed and are provided with attachment means for securing a supporting belt thereto.

6. The coupling ring of claim 1 in which said notch has an angular dimension approximating the maximum width of said tab portion.

7. The coupling ring of claim 1 in which said first rib means is provided with a rear surface facing said channel and lying along a generally radial plane and an inner surface facing inwardly toward the axis of said one coupling ring; said rear surface and said inner surface meeting along an edge.

8. The coupling ring of claim 7 in which said outer side wall of said one coupling ring has a generally cylindrical channel-facing inner surface and said notch of said first rib means includes an inwardly-facing surface portion having the same diameter as, and merging smoothly with, said cylindrical surface of said outer side wall.

9. The coupling ring of claim 7 in which said outer side wall of said one coupling ring has a generally cylindrical surface facing said channel; said one coupling ring including an arcuate shoulder within said notch; said shoulder having a maximum radial dimension measured from said cylindrical surface less than that of said rear surface of said first rib means.

10. The coupling ring of claim 9 in which said shoulder has a rounded surface when viewed in radial cross section.

11. The coupling ring of claim 1 in which a collection pouch having a stoma-receiving opening is secured thereto; said collection pouch being formed of thermoplastic material and having a wall portion defining a stoma-receiving opening and being heat sealed to said connecting wall of said ring about said opening.

12. A two-piece ostomy appliance comprising a collection pouch and adhesive faceplate means for peristomal attachment to a patient; said pouch having a stoma-receiving opening and a first coupling ring secured thereto about said opening; a second coupling ring connected to said faceplate means and detachably engagable with said first coupling ring; one of said coupling rings being of channel-shaped cross section and having spaced concentric inner and outer side walls and a connecting wall joining said side walls; the other of said coupling rings having substantially non-compressible annular insert means receivable in said channel and frictionally engagable with both of said side walls; said insert means including an axially-extending collar, a substantially non-deformable wedge body of toroidal shape, and an annular radially-extending pivot stem joining said collar and wedge body in concentric relation; said collar having an outwardly-extending annular bead and said wedge body having an inwardly-extending shoulder; said stem supporting said body for limited forward and rearward rocking movement about a pivot axis; said insert means having radial dimensions that expand when said body rocks forwardly and diminish when said body rocks rearwardly; wherein the improvement comprises said one coupling ring having first rib means projecting into said channel from said outer side wall and having second rib means projecting into said channel from said inner side wall; said first and second rib means being in direct opposition to each other and extending along a single plane normal to the axis of said one coupling ring; said first rib means being engagable with said bead of said collar and said second rib means being engagable with said shoulder of said wedge body to rock said body forwardly, thereby expanding the insert means and increasing resistance to uncoupling of said rings.

13. The two-piece ostomy appliance of claim 12 in which said side walls of said one coupling ring are of substantially equal length and define an entrance opening for the channel of said ring; said first and second rib means being located at said entrance opening.

14. The two-piece ostomy appliance of claim 12 in which said first rib means is provided with a rear surface facing said channel and lying along a generally radial plane and an inner surface facing inwardly toward the axis of said one coupling ring; said rear surface and said inner surface meeting along an edge.

15. The two-piece ostomy appliance of claim 14 in which said one coupling ring includes at least one tab portion projecting radially outwardly from said outer wall; said rear surface, said inner surface, and said edge being interrupted at the location of said tab portion to define a notch in said first rib means aligned with said tab portion.

16. The two-piece ostomy appliance of claim 15 in which said notch has a length approximating the width of said tab portion.

17. The two-piece ostomy appliance of claim 15 in which said notch has an angular dimension within the range of about 20 to 50 degrees.

18. The two-piece ostomy appliance of claim 15 in which said outer side wall of said one coupling ring has a generally cylindrical channel-facing inner surface and said notch of said first rib means includes an inwardly-facing surface portion having the same diameter as, and merging smoothly with, said cylindrical surface of said outer side wall.

19. The two-piece ostomy appliance of claim 15 in which said outer side wall of said one coupling ring has a generally cylindrical surface facing said channel; said one coupling ring including an arcuate shoulder within said notch; said shoulder having a maximum radial dimension measured from said cylindrical surface less than that of said rear surface of said first rib means.

20. The two-piece ostomy appliance of claim 19 in which said shoulder has a rounded surface when viewed in radial cross section.

21. The two-piece ostomy appliance of claims 15, 18, 19 or 20 in which said one coupling ring has a plurality of said tab portions and a plurality of said notches; said tab portions being circumferentially spaced apart and each having one of said plurality of notches aligned therewith.

22. The two-piece ostomy appliance of claim 21 in which said plurality of notches are spaced uniformly apart to define a plurality of rib portions of equal length therebetween.

23. The two-piece ostomy appliance of claim 21 in which two of said radially outwardly extending tab portions are diametrically disposed and are provided with attachment means for securing a supporting belt thereto.

* * * * *